US010119149B2

(12) United States Patent
Meade et al.

(10) Patent No.: US 10,119,149 B2
(45) Date of Patent: *Nov. 6, 2018

(54) USE OF DIG3 INSECTICIDAL CRYSTAL PROTEIN IN COMBINATION WITH CRY1AB FOR MANAGEMENT OF RESISTANCE IN EUROPEAN CORNBORER

(71) Applicant: Dow AgroSciences LLC, Indianapolis, IN (US)

(72) Inventors: Thomas Meade, Zionsville, IN (US); Kenneth Narva, Zionsville, IN (US); Nicholas P. Storer, Kensington, MD (US); Joel J. Sheets, Zionsville, IN (US); Aaron T. Woosley, Fishers, IN (US); Stephanie L. Burton, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 201 days.

This patent is subject to a terminal disclaimer.

(21) Appl. No.: 15/047,456

(22) Filed: Feb. 18, 2016

(65) Prior Publication Data

US 2016/0237452 A1 Aug. 18, 2016

Related U.S. Application Data

(63) Continuation-in-part of application No. 13/566,277, filed on Aug. 3, 2012.

(60) Provisional application No. 61/515,553, filed on Aug. 5, 2011.

(51) Int. Cl.
| | |
|---|---|
| *C12N 15/82* | (2006.01) |
| *A01H 5/10* | (2018.01) |
| *C07K 14/325* | (2006.01) |
| *C12N 15/32* | (2006.01) |
| *A01N 63/02* | (2006.01) |

(52) U.S. Cl.
CPC ......... *C12N 15/8286* (2013.01); *A01N 63/02* (2013.01); *C07K 14/325* (2013.01); *Y02A 40/162* (2018.01)

(58) Field of Classification Search
CPC .................... C12N 15/8286; C07K 14/325
See application file for complete search history.

(56) References Cited

U.S. PATENT DOCUMENTS

| | | | |
|---|---|---|---|
| 5,628,995 A | 5/1997 | Peferoen et al. | |
| 5,908,970 A | 6/1999 | Van Mellaert et al. | |
| 6,121,014 A | 9/2000 | Koziel et al. | |
| 8,304,604 B2 * | 11/2012 | Lira ..................... | C07K 14/325 435/320.1 |
| 9,006,520 B2 * | 4/2015 | Lira ..................... | C07K 14/325 435/418 |
| 2007/0006340 A1 | 1/2007 | Lang et al. | |
| 2010/0029725 A1 | 2/2010 | Cosgrove et al. | |
| 2010/0269223 A1 | 10/2010 | Lira et al. | |

FOREIGN PATENT DOCUMENTS

| | | |
|---|---|---|
| CN | 101568641 | 10/2009 |
| RU | 2210593 | 8/2003 |
| WO | WO 2011/075584 | 6/2011 |
| WO | WO 2011/075590 | 6/2011 |
| WO | WO 2011/084630 | 7/2011 |
| WO | WO 2011/084631 | 7/2011 |

OTHER PUBLICATIONS

Bohorova et al (TheorAppl Genet (2001) 103: 817-826).*
Ho et al (Crop Science, Mar./Apr. 2006; 46: 781-789).*
Bravo et al (GB vol. 26 No. 10 (Oct. 1, 2008) pp. 573-579).*
Bates et al (Nature Biotechnology vol. 23 No. 1 Jan. 2005).*
Bates et al., Nature Biotechnology, vol. 23, No. 1, (Jan. 2005).
Bohorova et al., "Novel synthetic Bacillus thuringiensiscry1B gene and the cry1B-cry1Ab translational fusion confer resistance to southwestern corn borer, sugarcane borer and fall armyworm in transgenic tropical maize," Theoretical and Applied Genetics, 2001, vol. 103, pp. 817-826.
Bravo et al., "How to cope with insect resistance to Bt toxins," Trends in Biotechnology, Elsevier Publications Cambridge, GB vol. 26 No. 10 (Oct. 1, 2008) pp. 573-579 pyramiding or Cry genes stacking; p. 576.
GenBank Accession AAM93496—first available online Aug. 13, 2002.
Ho et al., Crop Science, 46: 781-789 (Mar./Apr. 2006).
Tao et al., "Expression of plant protein phosphatase 2C interferes with nuclear import of the Agrobacterium T-complex protein VirD2," PNAS, 101(14): 5164-5169 (Apr. 6, 2004).

* cited by examiner

*Primary Examiner* — Lee A Visone
(74) *Attorney, Agent, or Firm* — Barnes & Thornburg LLP (57) ABSTRACT

The subject invention includes methods and plants for controlling European corn borer, said plants comprising a Cry1Ab insecticidal protein and a DIG-3 insecticidal protein to delay or prevent development of resistance by the insect.

23 Claims, 1 Drawing Sheet
Specification includes a Sequence Listing.

SEQUENCE LISTING

```
<160> NUMBER OF SEQ ID NOS: 2

<210> SEQ ID NO 1
<211> LENGTH: 1155
<212> TYPE: PRT
<213> ORGANISM: Bacillus thuringiensis

<400> SEQUENCE: 1

Met Asp Asn Asn Pro Asn Ile Asn Glu Cys Ile Pro Tyr Asn Cys Leu
```

-continued

```
1               5               10              15

Ser Asn Pro Glu Val Glu Val Leu Gly Gly Glu Arg Ile Glu Thr Gly
            20                  25                  30

Tyr Thr Pro Ile Asp Ile Ser Leu Ser Leu Thr Gln Phe Leu Leu Ser
            35                  40                  45

Glu Phe Val Pro Gly Ala Gly Phe Val Leu Gly Leu Val Asp Ile Ile
    50                  55                  60

Trp Gly Ile Phe Gly Pro Ser Gln Trp Asp Ala Phe Leu Val Gln Ile
65                  70                  75                  80

Glu Gln Leu Ile Asn Gln Arg Ile Glu Glu Phe Ala Arg Asn Gln Ala
                85                  90                  95

Ile Ser Arg Leu Glu Gly Leu Ser Asn Leu Tyr Gln Ile Tyr Ala Glu
                100                 105                 110

Ser Phe Arg Glu Trp Glu Ala Asp Pro Thr Asn Pro Ala Leu Arg Glu
            115                 120                 125

Glu Met Arg Ile Gln Phe Asn Asp Met Asn Ser Ala Leu Thr Thr Ala
            130                 135                 140

Ile Pro Leu Phe Ala Val Gln Asn Tyr Gln Val Pro Leu Leu Ser Val
145                 150                 155                 160

Tyr Val Gln Ala Ala Asn Leu His Leu Ser Val Leu Arg Asp Val Ser
                165                 170                 175

Val Phe Gly Gln Arg Trp Gly Phe Asp Ala Ala Thr Ile Asn Ser Arg
            180                 185                 190

Tyr Asn Asp Leu Thr Arg Leu Ile Gly Asn Tyr Thr Asp Tyr Ala Val
            195                 200                 205

Arg Trp Tyr Asn Thr Gly Leu Glu Arg Val Trp Gly Pro Asp Ser Arg
            210                 215                 220

Asp Trp Val Arg Tyr Asn Gln Phe Arg Arg Glu Leu Thr Leu Thr Val
225                 230                 235                 240

Leu Asp Ile Val Ala Leu Phe Pro Asn Tyr Asp Ser Arg Arg Tyr Pro
                245                 250                 255

Ile Arg Thr Val Ser Gln Leu Thr Arg Glu Ile Tyr Thr Asn Pro Val
                260                 265                 270

Leu Glu Asn Phe Asp Gly Ser Phe Arg Gly Ser Ala Gln Gly Ile Glu
            275                 280                 285

Arg Ser Ile Arg Ser Pro His Leu Met Asp Ile Leu Asn Ser Ile Thr
290                 295                 300

Ile Tyr Thr Asp Ala His Arg Gly Tyr Tyr Tyr Trp Ser Gly His Gln
305                 310                 315                 320

Ile Met Ala Ser Pro Val Gly Phe Ser Gly Pro Glu Phe Thr Phe Pro
            325                 330                 335

Leu Tyr Gly Thr Met Gly Asn Ala Ala Pro Gln Gln Arg Ile Val Ala
            340                 345                 350

Gln Leu Gly Gln Gly Val Tyr Arg Thr Leu Ser Ser Thr Leu Tyr Arg
            355                 360                 365

Arg Pro Phe Asn Ile Gly Ile Asn Asn Gln Gln Leu Ser Val Leu Asp
    370                 375                 380

Gly Thr Glu Phe Ala Tyr Gly Thr Ser Ser Asn Leu Pro Ser Ala Val
385                 390                 395                 400

Tyr Arg Lys Ser Gly Thr Val Asp Ser Leu Asp Glu Ile Pro Pro Gln
                405                 410                 415

Asn Asn Asn Val Pro Pro Arg Gln Gly Phe Ser His Arg Leu Ser His
            420                 425                 430
```

```
Val Ser Met Phe Arg Ser Gly Phe Ser Asn Ser Ser Val Ser Ile Ile
        435                 440                 445

Arg Ala Pro Met Phe Ser Trp Ile His Arg Ser Ala Glu Phe Asn Asn
450                 455                 460

Ile Ile Pro Ser Ser Gln Ile Thr Gln Ile Pro Leu Thr Lys Ser Thr
465                 470                 475                 480

Asn Leu Gly Ser Gly Thr Ser Val Val Lys Gly Pro Gly Phe Thr Gly
                485                 490                 495

Gly Asp Ile Leu Arg Arg Thr Ser Pro Gly Gln Ile Ser Thr Leu Arg
                500                 505                 510

Val Asn Ile Thr Ala Pro Leu Ser Gln Arg Tyr Arg Val Arg Ile Arg
                515                 520                 525

Tyr Ala Ser Thr Thr Asn Leu Gln Phe His Thr Ser Ile Asp Gly Arg
                530                 535                 540

Pro Ile Asn Gln Gly Asn Phe Ser Ala Thr Met Ser Ser Gly Ser Asn
545                 550                 555                 560

Leu Gln Ser Gly Ser Phe Arg Thr Val Gly Phe Thr Thr Pro Phe Asn
                565                 570                 575

Phe Ser Asn Gly Ser Ser Val Phe Thr Leu Ser Ala His Val Phe Asn
                580                 585                 590

Ser Gly Asn Glu Val Tyr Ile Asp Arg Ile Glu Phe Val Pro Ala Glu
                595                 600                 605

Val Thr Phe Glu Ala Glu Tyr Asp Leu Glu Arg Ala Gln Lys Ala Val
                610                 615                 620

Asn Glu Leu Phe Thr Ser Ser Asn Gln Ile Gly Leu Lys Thr Asp Val
625                 630                 635                 640

Thr Asp Tyr His Ile Asp Gln Val Ser Asn Leu Val Glu Cys Leu Ser
                645                 650                 655

Asp Glu Phe Cys Leu Asp Glu Lys Lys Glu Leu Ser Glu Lys Val Lys
                660                 665                 670

His Ala Lys Arg Leu Ser Asp Glu Arg Asn Leu Leu Gln Asp Pro Asn
                675                 680                 685

Phe Arg Gly Ile Asn Arg Gln Leu Asp Arg Gly Trp Arg Gly Ser Thr
                690                 695                 700

Asp Ile Thr Ile Gln Gly Gly Asp Asp Val Phe Lys Glu Asn Tyr Val
705                 710                 715                 720

Thr Leu Leu Gly Thr Phe Asp Glu Cys Tyr Leu Thr Tyr Leu Tyr Gln
                725                 730                 735

Lys Ile Asp Glu Ser Lys Leu Lys Ala Tyr Thr Arg Tyr Gln Leu Arg
                740                 745                 750

Gly Tyr Ile Glu Asp Ser Gln Asp Leu Glu Ile Tyr Leu Ile Arg Tyr
                755                 760                 765

Asn Ala Lys His Glu Thr Val Asn Val Pro Gly Thr Gly Ser Leu Trp
770                 775                 780

Arg Leu Ser Ala Pro Ser Pro Ile Gly Lys Cys Ala His His Ser His
785                 790                 795                 800

His Phe Ser Leu Asp Ile Asp Val Gly Cys Thr Asp Leu Asn Glu Asp
                805                 810                 815

Leu Gly Val Trp Val Ile Phe Lys Ile Lys Thr Gln Asp Gly His Ala
                820                 825                 830

Arg Leu Gly Asn Leu Glu Phe Leu Glu Glu Lys Pro Leu Val Gly Glu
                835                 840                 845
```

```
Ala Leu Ala Arg Val Lys Arg Ala Glu Lys Lys Trp Arg Asp Lys Arg
    850                 855                 860
Glu Lys Leu Glu Trp Glu Thr Asn Ile Val Tyr Lys Glu Ala Lys Glu
865                 870                 875                 880
Ser Val Asp Ala Leu Phe Val Asn Ser Gln Tyr Asp Arg Leu Gln Ala
                885                 890                 895
Asp Thr Asn Ile Ala Met Ile His Ala Asp Lys Arg Val His Ser
                900                 905                 910
Ile Arg Glu Ala Tyr Leu Pro Glu Leu Ser Val Ile Pro Gly Val Asn
                915                 920                 925
Ala Ala Ile Phe Glu Glu Leu Glu Gly Arg Ile Phe Thr Ala Phe Ser
    930                 935                 940
Leu Tyr Asp Ala Arg Asn Val Ile Lys Asn Gly Asp Phe Asn Asn Gly
945                 950                 955                 960
Leu Ser Cys Trp Asn Val Lys Gly His Val Asp Val Glu Glu Gln Asn
                965                 970                 975
Asn His Arg Ser Val Leu Val Val Pro Glu Trp Glu Ala Glu Val Ser
                980                 985                 990
Gln Glu Val Arg Val Cys Pro Gly Arg Gly Tyr Ile Leu Arg Val Thr
                995                 1000                1005
Ala Tyr Lys Glu Gly Tyr Gly Glu Gly Cys Val Thr Ile His Glu
    1010                1015                1020
Ile Glu Asn Asn Thr Asp Glu Leu Lys Phe Ser Asn Cys Val Glu
    1025                1030                1035
Glu Glu Val Tyr Pro Asn Asn Thr Val Thr Cys Asn Asp Tyr Thr
    1040                1045                1050
Ala Thr Gln Glu Glu Tyr Gly Thr Tyr Thr Ser Arg Asn Arg
    1055                1060                1065
Gly Tyr Asp Gly Ala Tyr Glu Ser Asn Ser Ser Val Pro Ala Asp
    1070                1075                1080
Tyr Ala Ser Ala Tyr Glu Glu Lys Ala Tyr Thr Asp Gly Arg Arg
    1085                1090                1095
Asp Asn Pro Cys Glu Ser Asn Arg Gly Tyr Gly Asp Tyr Thr Pro
    1100                1105                1110
Leu Pro Ala Gly Tyr Val Thr Lys Glu Leu Glu Tyr Phe Pro Glu
    1115                1120                1125
Thr Asp Lys Val Trp Ile Glu Ile Gly Glu Thr Glu Gly Thr Phe
    1130                1135                1140
Ile Val Asp Ser Val Glu Leu Leu Leu Met Glu Glu
    1145                1150                1155

<210> SEQ ID NO 2
<211> LENGTH: 1256
<212> TYPE: PRT
<213> ORGANISM: Bacillus thuringiensis

<400> SEQUENCE: 2

Met Thr Ser Asn Arg Lys Asn Glu Asn Glu Ile Ile Asn Ala Leu Ser
1               5                   10                  15
Ile Pro Thr Val Ser Asn Pro Ser Thr Gln Met Asn Leu Ser Pro Asp
                20                  25                  30
Ala Arg Ile Glu Asp Ser Leu Cys Val Ala Glu Val Asn Asn Ile Asp
            35                  40                  45
Pro Phe Val Ser Ala Ser Thr Val Gln Thr Gly Ile Asn Ile Ala Gly
        50                  55                  60
```

-continued

Arg Ile Leu Gly Val Leu Gly Val Pro Phe Ala Gly Gln Leu Ala Ser
65                  70                  75                  80

Phe Tyr Ser Phe Leu Val Gly Glu Leu Trp Pro Ser Gly Arg Asp Pro
            85                  90                  95

Trp Glu Ile Phe Leu Glu His Val Glu Gln Leu Ile Arg Gln Gln Val
            100                 105                 110

Thr Glu Asn Thr Arg Asn Thr Ala Ile Ala Arg Leu Glu Gly Leu Gly
            115                 120                 125

Arg Gly Tyr Arg Ser Tyr Gln Gln Ala Leu Glu Thr Trp Leu Asp Asn
130                 135                 140

Arg Asn Asp Ala Arg Ser Arg Ser Ile Ile Leu Glu Arg Tyr Val Ala
145                 150                 155                 160

Leu Glu Leu Asp Ile Thr Thr Ala Ile Pro Leu Phe Arg Ile Arg Asn
                165                 170                 175

Gln Glu Val Pro Leu Leu Met Val Tyr Ala Gln Ala Ala Asn Leu His
            180                 185                 190

Leu Leu Leu Leu Arg Asp Ala Ser Leu Phe Gly Ser Glu Trp Gly Thr
            195                 200                 205

Ala Ser Ser Asp Val Asn Gln Tyr Tyr Gln Gln Ile Arg Tyr Thr
210                 215                 220

Glu Glu Tyr Ser Asn His Cys Val Gln Trp Tyr Asn Thr Gly Leu Asn
225                 230                 235                 240

Asn Leu Arg Gly Thr Asn Ala Glu Ser Trp Val Arg Tyr Asn Gln Phe
                245                 250                 255

Arg Arg Asp Leu Thr Leu Gly Val Leu Asp Leu Val Ala Leu Phe Pro
            260                 265                 270

Ser Tyr Asp Thr Arg Thr Tyr Pro Ile Asn Thr Ser Ala Gln Leu Thr
            275                 280                 285

Arg Glu Val Tyr Thr Asp Ala Ile Gly Thr Val His Pro Ser Gln Ala
            290                 295                 300

Phe Ala Ser Thr Thr Trp Phe Asn Asn Asn Ala Pro Ser Phe Ser Ala
305                 310                 315                 320

Ile Glu Ala Ala Val Ile Arg Pro Pro His Leu Leu Asp Phe Pro Glu
                325                 330                 335

Gln Leu Thr Ile Tyr Ser Thr Leu Ser Arg Trp Ser Asn Thr Gln Phe
            340                 345                 350

Met Asn Ile Trp Ala Gly His Arg Leu Glu Ser Arg Pro Ile Ala Gly
            355                 360                 365

Ser Leu Asn Thr Ser Thr Gln Gly Ser Thr Asn Thr Ser Ile Asn Pro
            370                 375                 380

Val Thr Leu Gln Phe Thr Ser Arg Asp Ile Tyr Arg Thr Glu Ser Leu
385                 390                 395                 400

Ala Gly Leu Asn Ile Phe Ile Thr Gln Pro Val Asn Gly Val Pro Trp
                405                 410                 415

Val Arg Phe Asn Trp Arg Asn Pro Leu Asn Ser Leu Arg Gly Ser Leu
            420                 425                 430

Leu Tyr Thr Ile Gly Tyr Thr Gly Val Gly Thr Gln Leu Gln Asp Ser
            435                 440                 445

Glu Thr Glu Leu Pro Pro Glu Thr Thr Glu Arg Pro Asn Tyr Glu Ser
            450                 455                 460

Tyr Ser His Arg Leu Ser His Ile Gly Leu Ile Ser Ser Ser His Val
465                 470                 475                 480

```
Arg Ala Leu Val Tyr Ser Trp Thr His Arg Ser Ala Asp Arg Thr Asn
                485                 490                 495

Thr Ile Gly Pro Asn Arg Ile Thr Gln Ile Pro Ala Val Lys Gly Arg
            500                 505                 510

Phe Leu Phe Asn Gly Ser Val Ile Ser Gly Pro Gly Phe Thr Gly Gly
        515                 520                 525

Asp Val Val Arg Leu Asn Arg Asn Gly Asn Ile Gln Asn Arg Gly
    530                 535                 540

Tyr Ile Glu Val Pro Ile Gln Phe Thr Ser Ser Thr Arg Tyr Arg
545                 550                 555                 560

Val Arg Val Arg Tyr Ala Ser Val Thr Ser Ile Glu Leu Asn Val Asn
                565                 570                 575

Trp Gly Asn Ser Ser Ile Phe Thr Asn Thr Leu Pro Ala Thr Ala Ala
            580                 585                 590

Ser Leu Asp Asn Leu Gln Ser Gly Asp Phe Gly Tyr Val Glu Ile Asn
        595                 600                 605

Asn Ala Phe Thr Ser Ala Thr Gly Asn Ile Val Gly Val Arg Asn Phe
    610                 615                 620

Ser Ala Asn Ala Glu Val Ile Ile Asp Arg Phe Glu Phe Ile Pro Val
625                 630                 635                 640

Thr Ala Thr Phe Glu Ala Lys Tyr Asp Leu Glu Arg Ala Gln Lys Ala
                645                 650                 655

Val Asn Ala Leu Phe Thr Ser Thr Asn Pro Arg Arg Leu Lys Thr Asp
            660                 665                 670

Val Thr Asp Tyr His Ile Asp Gln Val Ser Asn Leu Val Val Cys Leu
        675                 680                 685

Ser Asp Glu Phe Cys Leu Asp Glu Lys Arg Glu Leu Phe Glu Lys Val
    690                 695                 700

Lys Tyr Ala Lys Arg Leu Ser Asp Glu Arg Asn Leu Leu Gln Asp Pro
705                 710                 715                 720

Asn Phe Thr Phe Ile Asn Gly Gln Pro Ser Phe Ala Ser Ile Asp Gly
                725                 730                 735

Gln Ser Asn Phe Thr Ser Ile Asn Glu Leu Ser Asn His Gly Trp Trp
            740                 745                 750

Gly Ser Ala Asn Val Thr Ile Gln Glu Gly Asn Asp Val Phe Lys Glu
        755                 760                 765

Asn Tyr Val Thr Leu Pro Gly Thr Phe Asn Glu Cys Tyr Pro Asn Tyr
    770                 775                 780

Leu Tyr Gln Lys Ile Gly Glu Ser Glu Leu Lys Ala Tyr Thr Arg Tyr
785                 790                 795                 800

Gln Leu Arg Gly Tyr Ile Glu Asp Ser Gln Asp Leu Glu Ile Tyr Leu
                805                 810                 815

Ile Arg Tyr Asn Ala Lys His Glu Thr Leu Asn Val Pro Gly Thr Glu
            820                 825                 830

Ser Leu Trp Pro Leu Ser Val Glu Ser Pro Ile Gly Arg Cys Gly Glu
        835                 840                 845

Pro Asn Arg Cys Ala Pro His Phe Gly Trp Asn Pro Asp Leu Asp Cys
    850                 855                 860

Ser Cys Arg Asp Arg Glu Lys Cys Ala His His Ser His His Phe Thr
865                 870                 875                 880

Leu Asp Ile Asp Val Gly Cys Thr Asp Leu Gln Glu Asp Leu Gly Val
                885                 890                 895

Trp Val Val Phe Lys Ile Lys Thr Gln Glu Gly Tyr Ala Arg Leu Gly
```

```
                    900             905             910
Asn Leu Glu Phe Ile Glu Glu Lys Pro Leu Ile Gly Glu Ala Leu Ser
            915             920             925

Arg Val Lys Arg Ala Glu Lys Lys Trp Arg Asp Lys Arg Glu Lys Leu
    930             935             940

Gln Val Glu Thr Lys Arg Val Tyr Ile Asp Ala Lys Glu Ala Val Asp
945             950             955             960

Ala Leu Phe Val Asp Ser Gln Tyr Asp Arg Leu Gln Ala Asp Thr Asn
                965             970             975

Ile Gly Met Ile His Ala Ala Asp Arg Leu Val His Arg Ile His Glu
            980             985             990

Ala Tyr Leu Pro Glu Leu Pro Phe Ile Pro Gly Ile Asn Val Val Ile
            995             1000            1005

Phe Glu Glu Leu Glu Asn Arg Ile Ser Thr Ala Phe Ser Leu Tyr
    1010            1015            1020

Asp Ala Arg Asn Val Ile Lys Asn Gly Asp Phe Asn Asn Gly Leu
    1025            1030            1035

Thr Cys Trp Asn Val Lys Gly His Val Glu Val Gln Gln Leu Asn
    1040            1045            1050

Asn His Arg Ser Val Leu Val Ile Pro Glu Trp Glu Ala Glu Val
    1055            1060            1065

Ser Gln Lys Val Arg Val Cys Pro Gly Arg Gly Tyr Ile Leu Arg
    1070            1075            1080

Val Thr Ala Tyr Lys Glu Gly Tyr Gly Glu Gly Cys Val Thr Ile
    1085            1090            1095

His Glu Val Asp Asn Asn Thr Asp Gln Leu Lys Phe Ser Asn Cys
    1100            1105            1110

Glu Lys Gly Gln Val Tyr Pro Gly Asn Thr Ile Ala Cys Asn Asp
    1115            1120            1125

Tyr Asn Lys Asn His Gly Ala Asn Ala Cys Ser Ser Arg Asn Arg
    1130            1135            1140

Gly Tyr Asp Glu Phe Tyr Gly Asn Thr Pro Ala Asp Tyr Ser Ala
    1145            1150            1155

Asn Gln Lys Glu Tyr Gly Gly Ala Tyr Thr Ser His Asn His Ala
    1160            1165            1170

Tyr Gly Glu Ser Tyr Glu Ser Asn Ser Ser Ile Pro Ala Asp Tyr
    1175            1180            1185

Ala Pro Val Tyr Glu Glu Ala Tyr Thr His Gly Arg Arg Gly
    1190            1195            1200

Asn Ser Cys Glu Tyr Asn Arg Gly Tyr Thr Pro Leu Pro Ala Gly
    1205            1210            1215

Tyr Val Thr Ala Glu Leu Glu Tyr Phe Pro Glu Thr Asp Thr Val
    1220            1225            1230

Trp Val Glu Ile Gly Glu Thr Glu Gly Thr Phe Ile Val Asp Asn
    1235            1240            1245

Val Glu Leu Leu Leu Met Glu Glu
    1250            1255
```

USE OF DIG3 INSECTICIDAL CRYSTAL PROTEIN IN COMBINATION WITH CRY1AB FOR MANAGEMENT OF RESISTANCE IN EUROPEAN CORNBORER

CROSS-REFERENCE TO A RELATED APPLICATION

The subject application is a continuation-in-part of U.S. application Ser. No. 13/566,277, filed Aug. 3, 2012, which claims priority to U.S. provisional application Ser. No. 61/515,553, filed Aug. 5, 2011, the disclosures of each of which are incorporated herein by reference in their entireties.

BACKGROUND OF THE INVENTION

Humans grow corn for food and energy applications. Humans also grow many other crops, including soybeans and cotton. Insects eat and damage plants and thereby undermine these human efforts. Billions of dollars are spent each year to control insect pests and additional billions are lost to the damage they inflict. Synthetic organic chemical insecticides have been the primary tools used to control insect pests but biological insecticides, such as the insecticidal proteins derived from *Bacillus thuringiensis* (Bt), have played an important role in some areas. The ability to produce insect-resistant plants through transformation with Bt insecticidal protein genes has revolutionized modern agriculture and heightened the importance and value of insecticidal proteins and their genes.

Several Bt proteins have been used to create the insect-resistant transgenic plants that have been successfully registered and commercialized to date. These include Cry1Ab, Cry1Ac, Cry1F and Cry3Bb in corn, Cry1Ac and Cry2Ab in cotton, and Cry3A in potato.

The commercial products expressing these proteins express a single protein except in cases where the combined insecticidal spectrum of 2 proteins is desired (e.g., Cry1Ab and Cry3Bb in corn combined to provide resistance to lepidopteran pests and rootworm, respectively) or where the independent action of the proteins makes them useful as a tool for delaying the development of resistance in susceptible insect populations (e.g., Cry1Ac and Cry2Ab in cotton combined to provide resistance management for tobacco budworm). SMART STAX is a commercial product that incorporates several Cry proteins. See also U.S. Patent Application Publication No. 2008/0311096, which relates in part to Cry1Ab for controlling Cry1F-resistant European corn borer (ECB; *Ostrinia nubilalis* (Hübner)). U.S. Patent Application Publication No. 2010/0269223 relates to DIG-3.

The rapid and widespread adoption of insect-resistant transgenic plants has given rise to the concern that pest populations will develop resistance to the insecticidal proteins produced by these plants. Several strategies have been suggested for preserving the utility of Bt-based insect resistance traits which include deploying proteins at a high dose in combination with a refuge, and alternation with, or co-deployment of, different toxins (McGaughey et al. (1998), "B.t. Resistance Management," *Nature Biotechnol.* 16:144-146).

The proteins selected for use in an insect resistant management (IRM) stack need to exert their insecticidal effect independently so that resistance developed to one protein does not confer resistance to the second protein (i.e., there is not cross resistance to the proteins). If, for example, a pest population selected for resistance to "Protein A" is sensitive to "Protein B", one would conclude that there is not cross resistance and that a combination of Protein A and Protein B would be effective in delaying resistance to Protein A alone.

In the absence of resistant insect populations, assessments can be made based on other characteristics presumed to be related to mechanism of action and cross-resistance potential. The utility of receptor-mediated binding in identifying insecticidal proteins likely to not exhibit cross resistance has been suggested (van Mellaert et al. 1999). The key predictor of lack of cross resistance inherent in this approach is that the insecticidal proteins do not compete for receptors in a sensitive insect species.

In the event that two Bt toxins compete for the same receptor in an insect, then if that receptor mutates in that insect so that one of the toxins no longer binds to that receptor and thus is no longer insecticidal against the insect, it might be the case that the insect will also be resistant to the second toxin (which competitively bound to the same receptor). That is, the insect is cross-resistant to both Bt toxins. However, if two toxins bind to two different receptors, this could be an indication that the insect would not be simultaneously resistant to those two toxins.

Additional Cry toxins are listed at the website of the official B.t. nomenclature committee (Crickmore et al.; lifesci.sussex.ac.uk/home/Neil_Crickmore/Bt/). There are currently nearly 60 main groups of "Cry" toxins (Cry1-Cry59), with additional Cyt toxins and VIP toxins and the like. Many of each numeric group have capital-letter subgroups, and the capital letter subgroups have lower-cased letter sub-subgroups. (Cry1 has A-L, and Cry1A has a-i, for example).

BRIEF SUMMARY OF THE INVENTION

The subject invention relates in part to the surprising discovery that DIG-3 and Cry1Ab do not compete for binding to sites in European corn borer (ECB; *Ostrinia nubilalis* (Hübner)) gut cell membrane preparations. As one skilled in the art will recognize with the benefit of this disclosure, plants that produce both of these proteins (including insecticidal portions of the full-length proteins) can be used to delay or prevent the development of resistance to either of these insecticidal proteins alone. Corn is a preferred plant for use according to the subject invention. ECB is the preferred target insect for the subject pair of toxins.

Thus, the subject invention relates in part to the use of a Cry1Ab protein in combination with a DIG-3 protein. Plants (and acreage planted with such plants) that produce both of these proteins are included within the scope of the subject invention.

The subject invention also relates in part to triple stacks or "pyramids" of three (or more) toxins, with Cry1Ab and DIG-3 being the base pair. In some preferred pyramid embodiments, the combination of the selected toxins provides three sites of action against ECB. Some preferred "three sites of action" pyramid combinations include the subject base pair of proteins plus Cry1F as the third protein for targeting ECB. (It was known from US 2008 0311096 that Cry1Ab is effective against Cry1Fa-resistant ECB.) This particular triple stack, for example, would, according to the subject invention, advantageously and surprisingly provide three sites of action against ECB. This can help to reduce or eliminate the requirement for refuge acreage.

Although the subject invention is disclosed herein as a base pair of toxins, Cry1Ab and DIG-3, which, either together as a pair or in a "pyramid" of three or more toxins, provide for insect-resistance against ECB in corn, it should be understood that other combinations with Cry1Ab and DIG-3 can be also used according to the subject invention, preferably in corn.

BRIEF DESCRIPTION OF THE SEQUENCES

SEQ ID NO:1 is the full-length Cry1Ab exemplified protein. (MR818)
SEQ ID NO:2 is the full-length DIG-3 exemplified protein.

DETAILED DESCRIPTION OF THE INVENTION

The subject invention relates in part to the surprising discovery that Cry1Ab and DIG-3 do not compete with each other for binding sites in the gut of the European corn borer (ECB; *Ostrinia nubilalis* (Hübner)) or the fall armyworms (FAW; *Spodoptera frugiperda*). Thus, a Cry1Ab protein can be used in combination with a DIG-3 protein, preferably in transgenic corn, to delay or prevent ECB from developing resistance to either of these proteins alone. The subject pair of proteins can be effective at protecting plants (such as maize plants) from damage by Cry-resistant ECB. That is, one use of the subject invention is to protect corn and other economically important plant species from damage and yield loss caused by ECB populations that could develop resistance to Cry1Ab or DIG-3.

The subject invention thus teaches an insect resistant management (IRM) stack comprising Cry1Ab and DIG-3 to prevent or mitigate the development of resistance by ECB to either or both of these proteins.

Further, although the subject invention, disclosed herein, teaches an IRM stack comprising Cry1Ab and DIG-3 for preventing resistance by ECB to either or both of these proteins, it is within the scope of the invention disclosed herein that one or both of Cry1Ab and DIG-3 may be adapted, either alone or in combination, to prevent resistance by FAW to either or both of these proteins.

The present invention provides compositions for controlling lepidopteran pests comprising cells that produce a Cry1Ab core toxin-containing protein and a DIG-3 core toxin-containing protein.

The invention further comprises a host transformed to produce both a Cry1Ab insecticidal protein and a DIG-3 insecticidal protein, wherein said host is a microorganism or a plant cell. The subject polynucleotide(s) are preferably in a genetic construct under control of a non-*Bacillus-thuringiensis* promoter(s). The subject polynucleotides can comprise codon usage for enhanced expression in a plant.

It is additionally intended that the invention provides a method of controlling lepidopteran pests comprising contacting said pests or the environment of said pests with an effective amount of a composition that contains a Cry1Ab insecticidal protein and further contains a DIG-3 insecticidal protein.

An embodiment of the invention comprises a maize plant comprising a plant-expressible gene encoding a DIG-3 core toxin-containing protein and a plant-expressible gene encoding a Cry1Ab core toxin-containing protein, and seed of such a plant.

A further embodiment of the invention comprises a maize plant wherein a plant-expressible gene encoding a DIG-3 insecticidal protein and a plant-expressible gene encoding a Cry1Ab insecticidal protein have been introgressed into said maize plant, and seed of such a plant.

As described in the Examples, competitive receptor binding studies using DIG-3 and radiolabeled Cry1Ab proteins show that the DIG-3 protein does not compete for binding in ECB tissues to which Cry1Ab binds. These results also indicate that the combination of Cry1Ab and DIG-3 proteins can be an effective means to mitigate the development of resistance in ECB populations to either of these proteins. Thus, based in part on the data described herein, co-production (stacking) of DIG-3 with Cry1Ab for high dose can be used in IRM stacks for controlling ECB.

Other proteins can be added to this pair. For example, the subject invention also relates in part to triple stacks or "pyramids" of three (or more) toxins, with Cry1Ab and DIG-3 being the base pair. In some preferred pyramid embodiments, the selected toxins have three separate sites of action against ECB. Some preferred "three sites of action" pyramid combinations include the subject base pair of proteins plus Cry1Fa as the third protein for targeting ECB. These particular triple stacks would, according to the subject invention, advantageously and surprisingly provide three sites of action against ECB. This can help to reduce or eliminate the requirement for refuge acreage. By "separate sites of action," it is meant any of the given proteins do not cause cross-resistance with each other.

Thus, one deployment option is to use the subject pair of proteins in combination with a third toxin/gene, and to use this triple stack to mitigate the development of resistance in ECB to any of these toxins. Accordingly, the subject invention also relates in part to triple stacks or "pyramids" of three (or more) toxins. In some preferred pyramid embodiments, the selected toxins have three separate sites of action against ECB.

Included among deployment options of the subject invention would be to use two, three, or more proteins of the subject proteins in crop-growing regions where ECB can (or is known to) develop resistant populations.

Cry1Fa is deployed in the Herculex® and SmartStax™ products, for example. The subject pair of genes (Cry1Ab and DIG-3) could be combined into, for example, a Cry1Fa product such as Herculex® and/or SmartStax™. Accordingly, the subject pair of proteins could be significant in reducing the selection pressure on these and other proteins. The subject pair of proteins could thus be used as in the three gene combinations for corn.

As discussed above, additional toxins/genes can also be added according to the subject invention. For example, for use of Cry1Ab with Cry1Be to target ECB, see WO 2011/084631. For use of Cry1Ab with Cry2Aa to target ECB, see WO 2011/075590. Thus, Cry1Be and/or Cry2Aa could be used (optionally with Cry1Fa) in multiple protein stacks with the subject pair of proteins.

Plants (and acreage planted with such plants) that produce any of the subject combinations of proteins are included within the scope of the subject invention. Additional toxins/genes can also be added, but the particular stacks discussed above advantageously and surprisingly provide multiple sites of action against ECB. This can help to reduce or eliminate the requirement for refuge acreage. A field thus planted of over ten acres is thus included within the subject invention.

GENBANK can also be used to obtain the sequences for any of the genes and proteins discussed herein. Patents can also be used. For example, U.S. Pat. Nos. 5,188,960 and 5,827,514 describe Cry1Fa core toxin containing proteins suitable for use in carrying out the present invention. U.S. Pat. No. 6,218,188 describes plant-optimized DNA sequences encoding Cry1Fa core toxin-containing proteins that are suitable for use in the present invention.

Insects related to ECB can also be targeted. These can include stem borers and/or stalk-boring insects. The southwestern corn borer (*Diatraea grandiosella*—of the suborder Heterocera) is one example. The sugarcane borer is also a *Diatraea* species (*Diatraea saccharalis*). Combinations of proteins described herein can be used to target larval stages of the target insect. Adult lepidopterans, for example, butterflies and moths, primarily feed on flower nectar and are a significant effector of pollination. Nearly all lepidopteran larvae, i.e., caterpillars, feed on plants, and many are serious pests. Caterpillars feed on or inside foliage or on the roots or stem of a plant, depriving the plant of nutrients and often destroying the plant's physical support structure. Additionally, caterpillars feed on fruit, fabrics, and stored grains and flours, ruining these products for sale or severely diminishing their value.

Some chimeric toxins of the subject invention comprise a full N-terminal core toxin portion of a Bt toxin and, at some point past the end of the core toxin portion, the protein has a transition to a heterologous protoxin sequence. The N-terminal, insecticidally active, toxin portion of a Bt toxin is referred to as the "core" toxin. The transition from the core toxin segment to the heterologous protoxin segment can occur at approximately the toxin/protoxin junction or, in the alternative, a portion of the native protoxin (extending past the core toxin portion) can be retained, with the transition to the heterologous protoxin portion occurring downstream.

Typical, full-length three domain B.t. Cry proteins are approximately 130 kDa to 150 kDa. Cry1Ab is one example. DIG-3 is also a three-domain toxin—approximately 142 kDa in size.

As an example, one chimeric toxin of the subject invention, is a full core toxin portion of Cry1Ab (approximately amino acids 1 to 601) and/or a heterologous protoxin (approximately amino acids 602 to the C-terminus). In one preferred embodiment, the portion of a chimeric toxin comprising the protoxin is derived from a Cry1Ab protein toxin. In a preferred embodiment, the portion of a chimeric toxin comprising the protoxin is derived from a Cry1Ab protein toxin.

A person skilled in this art will appreciate that Bt toxins (even within a certain class such as Cry1B) can vary to some extent in length and the precise location of the transition from core toxin portion to protoxin portion. Typical full-length Cry toxins are about 1150 to about 1200 amino acids in length. The transition from core toxin portion to protoxin portion will typically occur at between about 50% to about 60% of the full length toxin. The chimeric toxin of the subject invention will include the full expanse of this N-terminal core toxin portion. Thus, the chimeric toxin will comprise at least about 50% of the full length Cry1 protein. This will typically be at least about 590 amino acids (and could include 600-650 or so residues). With regard to the protoxin portion, the full expanse of the Cry1Ab protoxin portion extends from the end of the core toxin portion to the C-terminus of the molecule.

Genes and toxins. The genes and toxins useful according to the subject invention include not only the full length sequences disclosed but also fragments of these sequences, variants, mutants, and fusion proteins which retain the characteristic pesticidal activity of the toxins specifically exemplified herein. As used herein, the terms "variants" or "variations" of genes refer to nucleotide sequences which encode the same toxins or which encode equivalent toxins having pesticidal activity. As used herein, the term "equivalent toxins" refers to toxins having the same or essentially the same biological activity against the target pests as the claimed toxins.

As used herein, the boundaries represent approximately 95% (Cry1Ab's, for examples), 78% (Cry1A's and Cry1B's), and 45% (Cry1's) sequence identity, per "Revision of the Nomenclature for the *Bacillus thuringiensis* Pesticidal Crystal Proteins," N. Crickmore, D. R. Zeigler, J. Feitelson, E. Schnepf, J. Van Rie, D. Lereclus, J. Baum, and D. H. Dean. Microbiology and Molecular Biology Reviews (1998) Vol 62: 807-813. These cut offs can also be applied to the core toxins only.

It should be apparent to a person skilled in this art that genes encoding active toxins can be identified and obtained through several means. The specific genes or gene portions exemplified herein may be obtained from the isolates deposited at a culture depository. These genes, or portions or variants thereof, may also be constructed synthetically, for example, by use of a gene synthesizer. Variations of genes may be readily constructed using standard techniques for making point mutations. Also, fragments of these genes can be made using commercially available exonucleases or endonucleases according to standard procedures. For example, enzymes such as Bal31 or site-directed mutagenesis can be used to systematically cut off nucleotides from the ends of these genes. Genes that encode active fragments may also be obtained using a variety of restriction enzymes. Proteases may be used to directly obtain active fragments of these protein toxins.

Fragments and equivalents which retain the pesticidal activity of the exemplified toxins would be within the scope of the subject invention. Also, because of the redundancy of the genetic code, a variety of different DNA sequences can encode the amino acid sequences disclosed herein. It is well within the skill of a person trained in the art to create these alternative DNA sequences encoding the same, or essentially the same, toxins. These variant DNA sequences are within the scope of the subject invention. As used herein, reference to "essentially the same" sequence refers to sequences which have amino acid substitutions, deletions, additions, or insertions which do not materially affect pesticidal activity. Fragments of genes encoding proteins that retain pesticidal activity are also included in this definition.

A further method for identifying the genes encoding the toxins and gene portions useful according to the subject invention is through the use of oligonucleotide probes. These probes are detectable nucleotide sequences. These sequences may be detectable by virtue of an appropriate label or may be made inherently fluorescent as described in International Application No. WO93/16094. As is well known in the art, if the probe molecule and nucleic acid sample hybridize by forming a strong bond between the two molecules, it can be reasonably assumed that the probe and sample have substantial homology. Preferably, hybridization is conducted under stringent conditions by techniques well-known in the art, as described, for example, in Keller, G. H., M. M. Manak (1987) DNA Probes, Stockton Press, New York, N.Y., pp. 169-170. Some examples of salt concentrations and temperature combinations are as follows (in order of increasing stringency): 2×SSPE or SSC at room temperature; 1×SSPE or SSC at 42° C.; 0.1×SSPE or SSC at 42° C.; 0.1×SSPE or SSC at 65° C. Detection of the probe provides a means for determining in a known manner whether hybridization has occurred. Such a probe analysis provides a rapid method for identifying toxin-encoding genes of the subject invention. The nucleotide segments which are used as probes according to the invention can be synthesized using a DNA synthesizer and standard procedures. These nucleotide sequences can also be used as PCR primers to amplify genes of the subject invention.

Variant toxins. Certain toxins of the subject invention have been specifically exemplified herein. Since these toxins are merely exemplary of the toxins of the subject invention, it should be readily apparent that the subject invention comprises variant or equivalent toxins (and nucleotide sequences coding for equivalent toxins) having the same or similar pesticidal activity of the exemplified toxin. Equivalent toxins will have amino acid homology with an exemplified toxin. This amino acid homology will typically be greater than 75%, preferably be greater than 90%, and most preferably be greater than 95%. The amino acid homology will be highest in critical regions of the toxin which account for biological activity or are involved in the determination of three-dimensional configuration which ultimately is responsible for the biological activity. In this regard, certain amino acid substitutions are acceptable and can be expected if these substitutions are in regions which are not critical to activity or are conservative amino acid substitutions which do not affect the three-dimensional configuration of the molecule. For example, amino acids may be placed in the following classes: non-polar, uncharged polar, basic, and acidic. Conservative substitutions whereby an amino acid of one class is replaced with another amino acid of the same type fall within the scope of the subject invention so long as the substitution does not materially alter the biological activity of the compound. Below is a listing of examples of amino acids belonging to each class.

TABLE 1

Examples of Amino Acids within the Four Classes of Amino Acids

| Class of Amino Acid | Examples of Amino Acids |
| --- | --- |
| Nonpolar | Ala, Val, Leu, Ile, Pro, Met, Phe, Trp |
| Uncharged Polar | Gly, Ser, Thr, Cys, Tyr, Asn, Gln |
| Acidic | Asp, Glu |
| Basic | Lys, Arg, His |

In some instances, non-conservative substitutions can also be made. The critical factor is that these substitutions must not significantly detract from the biological activity of the toxin.

Recombinant hosts. The genes encoding the toxins of the subject invention can be introduced into a wide variety of microbial or plant hosts. Expression of the toxin gene results, directly or indirectly, in the intracellular production and maintenance of the pesticide. Conjugal transfer and recombinant transfer can be used to create a Bt strain that expresses both toxins of the subject invention. Other host organisms may also be transformed with one or both of the toxin genes then used to accomplish the synergistic effect. With suitable microbial hosts, e.g., *Pseudomonas*, the microbes can be applied to the situs of the pest, where they will proliferate and be ingested. The result is control of the pest. Alternatively, the microbe hosting the toxin gene can be treated under conditions that prolong the activity of the toxin and stabilize the cell. The treated cell, which retains the toxic activity, then can be applied to the environment of the target pest.

Where the Bt toxin gene is introduced via a suitable vector into a microbial host, and said host is applied to the environment in a living state, it is essential that certain host microbes be used. Microorganism hosts are selected which are known to occupy the "phytosphere" (phylloplane, phyllosphere, rhizosphere, and/or rhizoplane) of one or more crops of interest. These microorganisms are selected so as to be capable of successfully competing in the particular environment (crop and other insect habitats) with the wild-type microorganisms, provide for stable maintenance and expression of the gene expressing the polypeptide pesticide, and, desirably, provide for improved protection of the pesticide from environmental degradation and inactivation.

A large number of microorganisms are known to inhabit the phylloplane (the surface of the plant leaves) and/or the rhizosphere (the soil surrounding plant roots) of a wide variety of important crops. These microorganisms include bacteria, algae, and fungi. Of particular interest are microorganisms, such as bacteria, e.g., genera *Pseudomonas, Erwinia, Serratia, Klebsiella, Xanthomonas, Streptomyces, Rhizobium, Rhodopseudomonas, Methylophilius, Agrobactenum, Acetobacter, Lactobacillus, Arthrobacter, Azotobacter, Leuconostoc*, and *Alcaligenes*; fungi, particularly yeast, e.g., genera *Saccharomyces, Cryptococcus, Kluyveromyces, Sporobolomyces, Rhodotorula*, and *Aureobasidium*. Of particular interest are such phytosphere bacterial species as *Pseudomonas syringae, Pseudomonas fluorescens, Serratia marcescens, Acetobacter xylinum, Agrobactenium tumefaciens, Rhodopseudomonas spheroides, Xanthomonas campestris, Rhizobium melioti, Alcaligenes entrophus*, and *Azotobacter vinlandii*; and phytosphere yeast species such as *Rhodotorula rubra, R. glutinis, R. marina, R. aurantiaca, Cryptococcus albidus, C. diffluens, C. laurentii, Saccharomyces rosei, S. pretoriensis, S. cerevisiae, Sporobolomyces roseus, S. odorus, Kluyveromyces veronae*, and *Aureobasidium pollulans*. Of particular interest are the pigmented microorganisms.

A wide variety of methods is available for introducing a Bt gene encoding a toxin into a microorganism host under conditions which allow for stable maintenance and expression of the gene. These methods are well known to those skilled in the art and are described, for example, in U.S. Pat. No. 5,135,867, which is incorporated herein by reference.

Treatment of cells. *Bacillus thuringiensis* or recombinant cells expressing the Bt toxins can be treated to prolong the toxin activity and stabilize the cell. The pesticide microcapsule that is formed comprises the Bt toxin or toxins within a cellular structure that has been stabilized and will protect the toxin when the microcapsule is applied to the environment of the target pest. Suitable host cells may include either prokaryotes or eukaryotes, normally being limited to those cells which do not produce substances toxic to higher organisms, such as mammals. However, organisms which produce substances toxic to higher organisms could be used, where the toxic substances are unstable or the level of application sufficiently low as to avoid any possibility of toxicity to a mammalian host. As hosts, of particular interest will be the prokaryotes and the lower eukaryotes, such as fungi.

The cell will usually be intact and be substantially in the proliferative form when treated, rather than in a spore form, although in some instances spores may be employed.

Treatment of the microbial cell, e.g., a microbe containing the Bt toxin gene or genes, can be by chemical or physical means, or by a combination of chemical and/or physical means, so long as the technique does not deleteriously affect the properties of the toxin, nor diminish the cellular capability of protecting the toxin. Examples of chemical reagents are halogenating agents, particularly halogens of atomic no. 17-80. More particularly, iodine can be used under mild conditions and for sufficient time to achieve the desired results. Other suitable techniques include treatment with aldehydes, such as glutaraldehyde; anti-infectives, such as zephiran chloride and cetylpyridinium chloride; alcohols, such as isopropyl and ethanol; various histologic fixatives, such as Lugol iodine, Bouin's fixative, various acids and Helly's fixative (See: Humason, Gretchen L., Animal Tissue Techniques, W. H. Freeman and Company, 1967); or a combination of physical (heat) and chemical agents that preserve and prolong the activity of the toxin produced in the cell when the cell is administered to the host environment. Examples of physical means are short wavelength radiation such as gamma-radiation and X-radiation, freezing, UV irradiation, lyophilization, and the like. Methods for treatment of microbial cells are disclosed in U.S. Pat. Nos. 4,695,455 and 4,695,462, which are incorporated herein by reference.

The cells generally will have enhanced structural stability which will enhance resistance to environmental conditions. Where the pesticide is in a proform, the method of cell treatment should be selected so as not to inhibit processing of the proform to the mature form of the pesticide by the target pest pathogen. For example, formaldehyde will crosslink proteins and could inhibit processing of the proform of a polypeptide pesticide. The method of treatment should retain at least a substantial portion of the bio-availability or bioactivity of the toxin.

Characteristics of particular interest in selecting a host cell for purposes of production include ease of introducing the Bt gene or genes into the host, availability of expression systems, efficiency of expression, stability of the pesticide in the host, and the presence of auxiliary genetic capabilities. Characteristics of interest for use as a pesticide microcapsule include protective qualities for the pesticide, such as thick cell walls, pigmentation, and intracellular packaging or formation of inclusion bodies; survival in aqueous environments; lack of mammalian toxicity; attractiveness to pests for ingestion; ease of killing and fixing without damage to the toxin; and the like. Other considerations include ease of formulation and handling, economics, storage stability, and the like.

Growth of cells. The cellular host containing the Bt insecticidal gene or genes may be grown in any convenient nutrient medium, where the DNA construct provides a selective advantage, providing for a selective medium so that substantially all or all of the cells retain the Bt gene. These cells may then be harvested in accordance with conventional ways. Alternatively, the cells can be treated prior to harvesting.

The Bt cells producing the toxins of the invention can be cultured using standard art media and fermentation techniques. Upon completion of the fermentation cycle the bacteria can be harvested by first separating the Bt spores and crystals from the fermentation broth by means well known in the art. The recovered Bt spores and crystals can be formulated into a wettable powder, liquid concentrate, granules or other formulations by the addition of surfactants, dispersants, inert carriers, and other components to facilitate handling and application for particular target pests. These formulations and application procedures are all well known in the art.

Formulations. Formulated bait granules containing an attractant and spores, crystals, and toxins of the Bt isolates, or recombinant microbes comprising the genes obtainable from the Bt isolates disclosed herein, can be applied to the soil. Formulated product can also be applied as a seed-coating or root treatment or total plant treatment at later stages of the crop cycle. Plant and soil treatments of Bt cells may be employed as wettable powders, granules or dusts, by mixing with various inert materials, such as inorganic minerals (phyllosilicates, carbonates, sulfates, phosphates, and the like) or botanical materials (powdered corncobs, rice hulls, walnut shells, and the like). The formulations may include spreader-sticker adjuvants, stabilizing agents, other pesticidal additives, or surfactants. Liquid formulations may be aqueous-based or non-aqueous and employed as foams, gels, suspensions, emulsifiable concentrates, or the like. The ingredients may include rheological agents, surfactants, emulsifiers, dispersants, or polymers.

As would be appreciated by a person skilled in the art, the pesticidal concentration will vary widely depending upon the nature of the particular formulation, particularly whether it is a concentrate or to be used directly. The pesticide will be present in at least 1% by weight and may be 100% by weight. The dry formulations will have from about 1-95% by weight of the pesticide while the liquid formulations will generally be from about 1-60% by weight of the solids in the liquid phase. The formulations will generally have from about $10^2$ to about $10^4$ cells/mg. These formulations will be administered at about 50 mg (liquid or dry) to 1 kg or more per hectare.

The formulations can be applied to the environment of the lepidopteran pest, e.g., foliage or soil, by spraying, dusting, sprinkling, or the like.

Plant transformation. A preferred recombinant host for production of the insecticidal proteins of the subject invention is a transformed plant. Genes encoding Bt toxin proteins, as disclosed herein, can be inserted into plant cells using a variety of techniques which are well known in the art. For example, a large number of cloning vectors comprising a replication system in *Escherichia coli* and a marker that permits selection of the transformed cells are available for preparation for the insertion of foreign genes into higher plants. The vectors comprise, for example, pBR322, pUC series, M13mp series, pACYC184, inter alia. Accordingly, the DNA fragment having the sequence encoding the Bt toxin protein can be inserted into the vector at a suitable restriction site. The resulting plasmid is used for transformation into *E. coli*. The *E. coli* cells are cultivated in a suitable nutrient medium, then harvested and lysed. The plasmid is recovered. Sequence analysis, restriction analysis, electrophoresis, and other biochemical-molecular biological methods are generally carried out as methods of analysis. After each manipulation, the DNA sequence used can be cleaved and joined to the next DNA sequence. Each plasmid sequence can be cloned in the same or other plasmids. Depending on the method of inserting desired genes into the plant, other DNA sequences may be necessary. If, for example, the Ti or Ri plasmid is used for the transformation of the plant cell, then at least the right border, but often the right and the left border of the Ti or Ri plasmid T-DNA, has to be joined as the flanking region of the genes to be inserted. The use of T-DNA for the transformation of plant cells has been intensively researched and sufficiently described in EP 120 516, Lee and Gelvin (2008), Hoekema (1985), Fraley et al., (1986), and An et al., (1985), and is well established in the art.

Once the inserted DNA has been integrated in the plant genome, it is relatively stable. The transformation vector normally contains a selectable marker that confers on the transformed plant cells resistance to a biocide or an antibiotic, such as Bialaphos, Kanamycin, G418, Bleomycin, or Hygromycin, inter alia. The individually employed marker should accordingly permit the selection of transformed cells rather than cells that do not contain the inserted DNA.

A large number of techniques are available for inserting DNA into a plant host cell. Those techniques include transformation with T-DNA using *Agrobacterium tumefaciens* or *Agrobacterium rhizogenes* as transformation agent, fusion, injection, biolistics (microparticle bombardment), or electroporation as well as other possible methods. If Agrobacteria are used for the transformation, the DNA to be inserted has to be cloned into special plasmids, namely either into an intermediate vector or into a binary vector. The intermediate vectors can be integrated into the Ti or Ri plasmid by homologous recombination owing to sequences that are homologous to sequences in the T-DNA. The Ti or Ri plasmid also comprises the vir region necessary for the transfer of the T-DNA. Intermediate vectors cannot replicate themselves in Agrobacteria. The intermediate vector can be transferred into *Agrobacterium tumefaciens* by means of a helper plasmid (conjugation). Binary vectors can replicate themselves both in *E. coli* and in Agrobacteria. They comprise a selection marker gene and a linker or polylinker which are framed by the Right and Left T-DNA border regions. They can be transformed directly into Agrobacteria (Holsters et al., 1978). The *Agrobacterium* used as host cell is to comprise a plasmid carrying a vir region. The vir region is necessary for the transfer of the T-DNA into the plant cell. Additional T-DNA may be contained. The bacterium so transformed is used for the transformation of plant cells. Plant explants can advantageously be cultivated with *Agrobacterium tumefaciens* or *Agrobacterium rhizogenes* for the transfer of the DNA into the plant cell. Whole plants can then be regenerated from the infected plant material (for example, pieces of leaf, segments of stalk, roots, but also protoplasts or suspension-cultivated cells) in a suitable medium, which may contain antibiotics or biocides for selection. The plants so obtained can then be tested for the presence of the inserted DNA. No special demands are made of the plasmids in the case of injection and electroporation. It is possible to use ordinary plasmids, such as, for example, pUC derivatives.

The transformed cells grow inside the plants in the usual manner. They can form germ cells and transmit the transformed trait(s) to progeny plants. Such plants can be grown in the normal manner and crossed with plants that have the same transformed hereditary factors or other hereditary factors. The resulting hybrid individuals have the corresponding phenotypic properties.

In a preferred embodiment of the subject invention, plants will be transformed with genes wherein the codon usage has been optimized for plants. See, for example, U.S. Pat. No. 5,380,831, which is hereby incorporated by reference. While some truncated toxins are exemplified herein, it is well-known in the Bt art that 130 kDa-type (full-length) toxins have an N-terminal half that is the core toxin, and a C-terminal half that is the protoxin "tail." Thus, appropriate "tails" can be used with truncated/core toxins of the subject invention. See e.g. U.S. Pat. Nos. 6,218,188 and 6,673,990. In addition, methods for creating synthetic Bt genes for use in plants are known in the art (Stewart and Burgin, 2007). One non-limiting example of a preferred transformed plant is a fertile maize plant comprising a plant expressible gene encoding a Cry1Ab protein, and further comprising a second plant expressible gene encoding a Cry1Be protein.

Transfer (or introgression) of the Cry1Ab- and Cry1Be-determined trait(s) into inbred maize lines can be achieved by recurrent selection breeding, for example by backcrossing. In this case, a desired recurrent parent is first crossed to a donor inbred (the non-recurrent parent) that carries the appropriate gene(s) for the Cry1A- and Cry1Be-determined traits. The progeny of this cross is then mated back to the recurrent parent followed by selection in the resultant progeny for the desired trait(s) to be transferred from the non-recurrent parent. After three, preferably four, more preferably five or more generations of backcrosses with the recurrent parent with selection for the desired trait(s), the progeny will be heterozygous for loci controlling the trait(s) being transferred, but will be like the recurrent parent for most or almost all other genes (see, for example, Poehlman & Sleper (1995) Breeding Field Crops, 4th Ed., 172-175; Fehr (1987) Principles of Cultivar Development, Vol. 1: Theory and Technique, 360-376).

Insect Resistance Management (IRM) Strategies. Roush et al., for example, outlines two-toxin strategies, also called "pyramiding" or "stacking," for management of insecticidal transgenic crops. (The Royal Society. *Phil. Trans. R. Soc. Lond. B.* (1998) 353, 1777-1786).

On their website, the United States Environmental Protection Agency (epa.gov/oppbppd1/biopesticides/pips/bt_corn_refuge_2006.htm) publishes the following requirements for providing non-transgenic (i.e., non-B.t.) refuges (a section of non-Bt crops/corn) for use with transgenic crops producing a single Bt protein active against target pests.

"The specific structured requirements for corn borer-protected Bt (Cry1Ab or Cry1F) corn products are as follows:

Structured refuges: 20% non-Lepidopteran Bt corn refuge in Corn Belt; 50% non-Lepidopteran Bt refuge in Cotton Belt Blocks

- Internal (i.e., within the Bt field)
- External (i.e., separate fields within ½ mile (¼ mile if possible) of the Bt field to maximize random mating)

In-field Strips

- Strips must be at least 4 rows wide (preferably 6 rows) to reduce the effects of larval movement"

In addition, the National Corn Growers Association, on their website:

(ncga.com/insect-resistance-management-fact-sheet-bt-corn)

also provides similar guidance regarding the refuge requirements. For example:

Requirements of the Corn Borer IRM:

- Plant at least 20% of your corn acres to refuge hybrids
- In cotton producing regions, refuge must be 50%
- Must be planted within ½ mile of the refuge hybrids
- Refuge can be planted as strips within the Bt field; the refuge strips must be at least 4 rows wide
- Refuge may be treated with conventional pesticides only if economic thresholds are reached for target insect
- Bt-based sprayable insecticides cannot be used on the refuge corn Appropriate refuge must be planted on every farm with Bt corn"

As stated by Roush et al. (on pages 1780 and 1784 right column, for example), stacking or pyramiding of two different proteins each effective against the target pests and with little or no cross-resistance can allow for use of a smaller refuge. Roush suggests that for a successful stack, a refuge size of less than 10% refuge, can provide comparable resistance management to about 50% refuge for a single (non-pyramided) trait. For currently available pyramided Bt corn products, the U.S. Environmental Protection Agency requires significantly less (generally 5%) structured refuge of non-Bt corn be planted than for single trait products (generally 20%).

There are various ways of providing the IRM effects of a refuge, including various geometric planting patterns in the fields (as mentioned above) and in-bag seed mixtures, as discussed further by Roush et al. (supra), and U.S. Pat. No. 6,551,962.

The above percentages, or similar refuge ratios, can be used for the subject double or triple stacks or pyramids. For triple stacks with three sites of action against a single target pest, a goal would be zero refuge (or less than 5% refuge, for example). This is particularly true for commercial acreage—of over 10 acres for example.

All patents, patent applications, provisional applications, and publications referred to or cited herein are incorporated by reference in their entirety to the extent they are not inconsistent with the explicit teachings of this specification.

Unless specifically indicated or implied, the terms "a", "an", and "the" signify "at least one" as used herein.

Following are examples that illustrate procedures for practicing the invention. These examples should not be construed as limiting. All percentages are by weight and all solvent mixture proportions are by volume unless otherwise noted. All temperatures are in degrees Celsius.

EXAMPLES

Example 1

$^{125}$I Labeling of Cry1Ab Protein

Iodination of Cry1Ab core toxin. Cry1Ab toxin (SEQ ID NO:1) was trypsin activated and iodinated using Iodo-Beads (Pierce). Briefly, two Iodo-Beads were washed twice with 500 µl of phosphate buffered saline, PBS (20 mM sodium phosphate, 0.15 M NaCl, pH 7.5), and placed into a 1.5 ml centrifuge tube behind lead shielding. To this was added 100 µl of PBS. In a hood and through the use of proper radioactive handling techniques, 0.5 mCi Na$^{125}$I (17.4 Ci/mg, Amersham) was added to the PBS solution with the Iodo-Bead. The components were allowed to react for 5 minutes at room temperature, then 10 µg of highly pure truncated Cry1Ab protein was added to the solution and allowed to react for an additional 5 minutes. The reaction was terminated by removing the solution from the iodo-beads and applying it to a 0.5 ml desalting Zeba spin column (InVitrogen) equilibrated in 20 mM CAPS buffer, pH 10.5+1 mM DTT. The iodo-bead was washed twice with 10 µl of PBS each and the wash solution also applied to the desalting column The radioactive solution was eluted through the desalting column by centrifugation at 1,000×g for 2 min. Radio-purity of the radio-iodinated Cry1Ab was determined by SDS-PAGE, phosphor-imaging and gamma counting. Briefly, 2 µl of the radioactive protein was separated by SDS-PAGE using 4-20% tris glycine polyacrylamide gels (1 mm thick, InVitrogen). After separation, the gels were dried using a BioRad gel drying apparatus following the manufacturer's instructions. The dried gels were imaged by wrapping them in Mylar film (12 µm thick), and exposing them under a Molecular Dynamics storage phosphor screen (35 cm×43 cm), for 1 hour. The plates were developed using a Molecular Dynamics Storm 820 phosphorimager and the imaged analyzed using ImageQuant™ software. The specific activity was approximately 4 µCi/µg protein.

Example 2

BBMV Preparation Protocol

Preparation and Fractionation of Solubilized BBMV's. Last instar *Ostrinia nubilalis* larvae were fasted overnight and then dissected in the morning after chilling on ice for 15 minutes. The midgut tissue was removed from the body cavity, leaving behind the hindgut attached to the integument. The midgut was placed in 9× volume of ice cold homogenization buffer (300 mM mannitol, 17 mM tris. base, pH 7.5), supplemented with Protease Inhibitor Cocktail[1] (Sigma P-2714) diluted as recommended by the supplier. The tissue was homogenized with 15 strokes of a glass tissue homogenizer. BBMV's were prepared by the MgCl$_2$ precipitation method of Wolfersberger (1993). Briefly, an equal volume of a 24 mM MgCl$_2$ solution in 300 mM mannitol was mixed with the midgut homogenate, stirred for 5 minutes and allowed to stand on ice for 15 min. The solution was centrifuged at 2,500×g for 15 min at 4° C. The supernatant was saved and the pellet suspended into the original volume of 0.5-× diluted homogenization buffer and centrifuged again. The two supernatants were combined, centrifuged at 27,000×g for 30 min at 4° C. to form the BBMV fraction. The pellet was suspended into 10 ml homogenization buffer supplemented with protease inhibitors, and centrifuged again at 27,000×g for 30 min at 4° C. to wash the BBMV's. The resulting pellet was suspended into BBMV Storage Buffer (10 mM HEPES, 130 mM KCl, 10% glycerol, pH 7.4) to a concentration of about 3 mg/ml protein. Protein concentration was determined by using the Bradford method (1976) with bovine serum albumin (BSA) as the standard. Alkaline phosphatase determination was made prior to freezing the samples using the Sigma assay following manufacturer's instructions. The specific activity of this marker enzyme in the BBMV fraction typically increased 7-fold compared to that found in the midgut homogenate fraction. The BBMV's were aliquoted into 250 µl samples, flash frozen in liquid N$_2$ and stored at −80° C.

[1] Final concentration of cocktail components (in µM) are AEBSF (500), EDTA (250 mM), Bestatin (32), E-64 (0.35), Leupeptin (0.25), and Aprotinin (0.075).

Example 3

Method to Measure Binding of $^{125}$I Cry1Ab Protein to BBMV Proteins

Binding of $^{125}$I Cry1Ab Protein to BBMV's. To determine the optimal amount of BBMV protein to use in the binding assays, a saturation curve was generated. $^{125}$I radiolabeled Cry1Ab protein (0.5 nM) was incubated for 1 hour at 28° C. with various amounts of BBMV protein, ranging from 0-500 µg/ml in binding buffer (8 mM NaHPO$_4$, 2 mM KH$_2$PO$_4$, 150 mM NaCl, 0.1% bovine serum albumin, pH 7.4). Total volume was 0.5 ml. Bound $^{125}$I Cry1Ab protein was separated from unbound by sampling 150 µl of the reaction mixture in triplicate from a 1.5 ml centrifuge tube into a 500 µl centrifuge tube and centrifuging the samples at 14,000×g for 6 minutes at room temperature. The supernatant was gently removed, and the pellet gently washed three times with ice cold binding buffer. The bottom of the centrifuge containing the pellet was cut out and placed into a 13×75-mm glass culture tube. The samples were counted for 5 minutes each in the gamma counter. The counts contained in the sample were subtracted from background counts (reaction with out any protein) and was plotted versus BBMV protein concentration. The optimal amount of protein to use was determined to be 0.15 mg/ml of BBMV protein.

To determine the binding kinetics, a saturation curve was generated. Briefly, BBMV's (150 µg/ml) were incubated for 1 hr. at 28° C. with increasing concentrations of $^{125}$I Cry1Ab toxin, ranging from 0.01 to 10 nM. Total binding was determined by sampling 150 µl of each concentration in triplicate, centrifugation of the sample and counting as described above. Non-specific binding was determined in the same manner, with the addition of 1,000 nM of the homologous trypsinized non-radioactive Cry1Ab toxin added to the reaction mixture to saturate all non-specific receptor binding sites. Specific binding was calculated as the difference between total binding and non-specific binding.

Homologous (Cry1Ab) and heterologous (DIG-3) competition binding assays were conducted using 150 µg/ml BBMV protein and 0.5 nM of the $^{125}$I radiolabeled Cry1Ab protein. Cry1Ab and DIG-3 (SEQ ID NO:2) were trypsin activated and used as competitor proteins. The concentration of the competitive non-radiolabeled Cry1Ab or DIG-3 toxin added to the reaction mixture ranged from 0.03 to 1,000 nM and were added at the same time as the radioactive ligand, to assure true binding competition. Incubations were carried out for 1 hr. at 28° C. and the amount of $^{125}$I Cry1Ab protein bound to its receptor toxin measured as described above with non-specific binding subtracted. One hundred percent total binding was determined in the absence of any competitor ligand. Results were plotted on a semi-logarithmic plot as percent total specific binding versus concentration of competitive ligand added.

Example 4

Summary of Results

Figure 1:
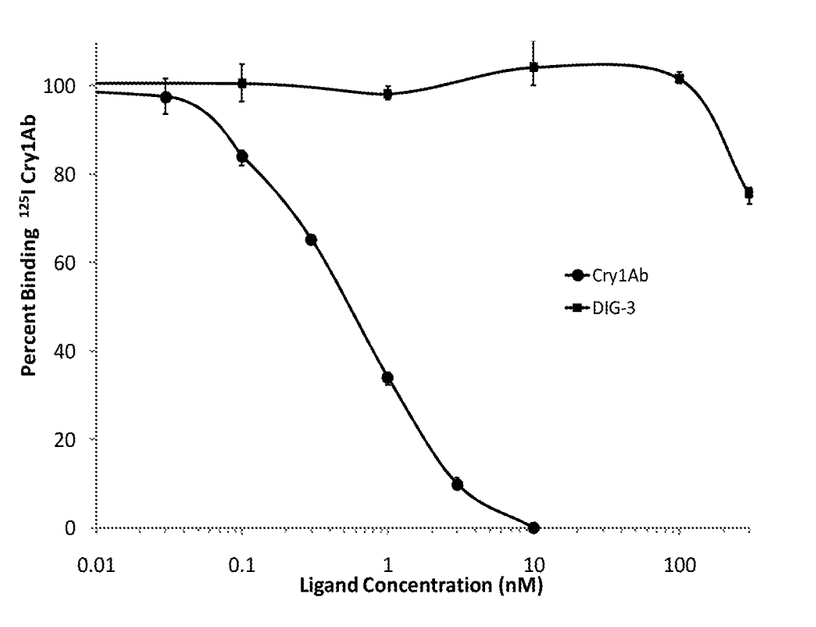
FIG. 1 shows percent specific binding of $^{125}$I Cry1Ab (0.5 nM) in BBMV's from *Ostrinia nubilalis* versus competition by unlabeled homologous Cry1Ab (●) and heterologous DIG-3 (■). The displacement curve for homologous competition by Cry1Ab results in a sigmoidal shaped curve showing 50% displacement of the radioligand at about 0.5 nM of Cry1Ab. DIG-3 does not displace any of the binding of $^{125}$I Cry1Ab from its binding site at concentrations of 100 nM or lower (200-fold higher than the concentration of $^{125}$I Cry1Ab in the assay). Only at 300 nM do we observe about 25% displacement of the biding of $^{125}$I Cry1Ab by DIG-3. These results show that DIG-3 does not effectively compete for the binding of Cry1Ab to receptor sites located in BBMV's from *Ostrinia nubilalis*.

FIG. 1 shows percent specific binding of $^{125}$I Cry1Ab (0.5 nM) in BBMV's from *Ostrinia nubilalis* versus competition by unlabeled homologous Cry1Ab (●) and heterologous DIG-3 (■). The displacement curve for homologous competition by Cry1Ab results in a sigmoidal shaped curve showing 50% displacement of the radioligand at about 0.5 nM of Cry1Ab. DIG-3 does not displace any of the binding of $^{125}$I Cry1Ab from its binding site at concentrations of 100 nM or lower (200-fold higher than the concentration of $^{125}$I Cry1Ab in the assay). Only at 300 nM do we observe about 25% displacement of the biding of $^{125}$I Cry1Ab by DIG-3. These results show that DIG-3 does not effectively compete for the binding of Cry1Ab to receptor sites located in BBMV's from *Ostrinia nubilalis*.

REFERENCE LIST

Heckel, D. G., Gahan, L. J., Baxter, S. W., Zhao, J. Z., Shelton, A. M., Gould, F., and Tabashnik, B. E. (2007). The diversity of Bt resistance genes in species of *Lepidoptera*. J Invertebr Pathol 95, 192-197.

Luo, K., Banks, D., and Adang, M. J. (1999). Toxicity, binding, and permeability analyses of four *bacillus thuringiensis* cry1 delta-endotoxins using brush border membrane vesicles of *spodoptera exigua* and *spodoptera frugiperda*. Appl. Environ. Microbiol. 65, 457-464.

Palmer, M., Buchkremer, M, Valeva, A, and Bhakdi, S. Cysteine-specific radioiodination of proteins with fluorescein maleimide. Analytical Biochemistry 253, 175-179. 1997. Ref Type: Journal (Full)

Sambrook, J. and Russell, D. W. (2001). Molecular Cloning: A Laboratory Manual. Cold Spring Harbor Laboratory).

Schlenz, M. L., Babcock, J. M., and Storer, N. P. Response of Cry1F-resistant and Susceptible European Corn Borer and Fall Armyworm Colonies to Cry1A.105 and Cry12Ab2. DAI 0830, 2008. Indianapolis, Dow AgroSciences. Derbi Report.

Sheets, J. J. and Storer, N. P. Analysis of Cry1Ac Binding to Proteins in Brush Border Membrane Vesicles of Corn Earworm Larvae (*Heleothis zea*). Interactions with Cry1F Proteins and Its Implication for Resistance in the Field. DAI-0417, 1-26. 2001. Indianapolis, Dow AgroSciences.

Tabashnik, B. E., Liu, Y. B., Finson, N., Masson, L., and Heckel, D. G. (1997). One gene in diamondback moth confers resistance to four *Bacillus thuringiensis* toxins. Proc. Natl. Acad. Sci. U.S.A 94, 1640-1644.

Tabashnik, B. E., Malvar, T., Liu, Y. B., Finson, N., Borthakur, D., Shin, B. S., Park, S. H., Masson, L., de Maagd, R. A., and Bosch, D. (1996). Cross-resistance of the diamondback moth indicates altered interactions with domain II of *Bacillus thuringiensis* toxins. Appl. Environ. Microbiol. 62, 2839-2844.

Tabashnik, B. E., Roush, R. T., Earle, E. D., and Shelton, A. M. (2000). Resistance to Bt toxins. Science 287, 42.

Wolfersberger, M. G. (1993). Preparation and partial characterization of amino acid transporting brush border membrane vesicles from the larval midgut of the gypsy moth (*Lymantria dispar*). Arch. Insect Biochem. Physiol 24, 139-147.

Xu, X., Yu, L., and Wu, Y. (2005). Disruption of a cadherin gene associated with resistance to Cry1Ac {delta}-endotoxin of *Bacillus thuringiensis* in *Helicoverpa armigera*. Appl Environ Microbiol 71, 948-954.

We claim:

1. A transgenic plant comprising a Cry1Ab polynucleotide encoding a Cry1Ab insecticidal protein, and a DIG-3 polynucleotide encoding a DIG-3 insecticidal protein having at least 95% sequence identity with SEQ ID NO:2.

2. The transgenic plant of claim 1, wherein said plant further comprises DNA encoding a third insecticidal protein selected from the group consisting of Cry1Fa, Cry1Be, and Cry2Aa.

3. The transgenic plant of claim 2, said plant further comprising DNA encoding a fourth insecticidal protein selected from the group consisting of Cry1Be and Cry2Aa where the third insecticidal protein is Cry1Fa.

4. A seed of the plant of claim 1, wherein said seed comprises the Cry1Ab polynucleotide encoding the Cry1Ab insecticidal protein and the DIG-3 polynucleotide encoding the DIG-3 insecticidal protein.

5. A plurality of plants comprising non-Bt refuge plants and the transgenic plants of claim 1, wherein said refuge plants comprise less than 40% of said plurality of plants.

6. The plurality of plants of claim 5, wherein said refuge plants comprise less than 30% of said plurality of plants.

7. The plurality of plants of claim 5, wherein said refuge plants comprise less than 20% of said plurality of plants.

8. The plurality of plants of claim 5, wherein said refuge plants comprise less than 10% of said plurality of plants.

9. The plurality of plants of claim 5, wherein said refuge plants comprise less than 5% of said plurality of plants.

10. The plurality of plants of claim 5, wherein said refuge plants are in blocks or strips.

11. A mixture of seeds comprising refuge seeds from non-Bt refuge plants and the seeds of claim 4, wherein said refuge seeds comprise less than 40% of all the seeds in the mixture.

12. The mixture of seeds of claim 11, wherein said refuge seeds comprise less than 30% of all the seeds in the mixture.

13. The mixture of seeds of claim 11, wherein said refuge seeds comprise less than 20% of all the seeds in the mixture.

14. The mixture of seeds of claim 11, wherein said refuge seeds comprise less than 10% of all the seeds in the mixture.

15. The mixture of seeds of claim 11, wherein said refuge seeds comprise less than 5% of all the seeds in the mixture.

16. A method of managing development of resistance to a Cry protein by an insect, said method comprising planting seeds to produce the plants of claim 5.

17. The plurality of plants of claim 5, wherein said plants occupy more than 10 acres.

18. The plant of claim 1, wherein said plant is selected from the group consisting of corn, soybeans, and cotton.

19. The plant of claim 18, wherein said plant is corn.

20. A non-totipotent plant cell comprising a Cry1Ab polynucleotide encoding a Cry1Ab insecticidal protein, and a DIG-3 polynucleotide encoding the DIG-3 insecticidal protein of SEQ ID NO:2.

21. A method of controlling a corn borer insect, wherein said method comprises contacting said insect or the environment of said insect with an effective amount of a composition that contains a Cry1Ab insecticidal protein and further contains the DIG-3 insecticidal protein of SEQ ID NO:2.

22. The method of claim 21, wherein said composition is a plurality of plant cells.

23. A method of producing the composition of claim 22, wherein said method comprises reproducing said cells.

* * * * *